United States Patent [19]

Goulter

[11] Patent Number: 5,618,277
[45] Date of Patent: Apr. 8, 1997

[54] CONDOM CATHETER WITH IMPROVED VALVE AND RETAINING MEANS

[76] Inventor: Victor H. Goulter, 485 Molimo Dr., San Francisco, Calif. 94127

[21] Appl. No.: 545,403

[22] Filed: Oct. 19, 1995

[51] Int. Cl.$^6$ ....................................... A61F 5/44
[52] U.S. Cl. .................. 604/349; 604/350; 604/353
[58] Field of Search ............................ 604/349–353; 128/844, 842, 760

[56] References Cited

U.S. PATENT DOCUMENTS

| | | | |
|---|---|---|---|
| 1,490,793 | 4/1924 | Ajamian et al. | 604/353 |
| 2,310,505 | 2/1943 | Blackburn et al. | 604/350 |
| 2,699,781 | 1/1955 | Koch | 604/352 |
| 3,405,714 | 10/1968 | Moss | 604/350 |
| 3,749,096 | 7/1973 | Donaldson | 604/353 |
| 5,002,541 | 3/1991 | Conkling et al. | 604/319 |
| 5,318,550 | 6/1994 | Cermak et al. | 604/350 |
| 5,380,312 | 1/1995 | Goulter | 604/352 |

FOREIGN PATENT DOCUMENTS

| | | |
|---|---|---|
| 637978 | 5/1950 | United Kingdom . |
| 2048680 | 12/1980 | United Kingdom . |

*Primary Examiner*—John G. Weiss
*Assistant Examiner*—David J. Cho
*Attorney, Agent, or Firm*—James J. Leary; Leary, Titus & Aiello

[57] ABSTRACT

A one-piece male incontinence device comprises a condom (30) having a first sheath section (32) and a second urine collecting compartment (42) divided by a skin shield (36) which incorporates a soft thread-reinforced non-return, non-invertible valve (38). Collecting compartment has a twist-around drain valve (52) or alternatively a ball-obturator drain valve (93). First sheath section (32) has friction-increasing internal surface in the form of finely spaced-apart ribs (54). Alternatively skin shield 36 can incorporate two non-return, non-inverting reinforced valves (86 and 88) placed to eliminate urine pooling (90). Alternative design catheter (79) comprises one-piece first sheath section and second urine collecting compartment divided by an insert (36) incorporating non-return valve or valves and skin shield which is placed and imperviously sealed therein. A garment (94) is provided for spinal injured patients for attaching thereto a condom catheter. A non-elastomeric, non-latex condom catheter (110) is provided for users who are allergic to latex products.

26 Claims, 6 Drawing Sheets

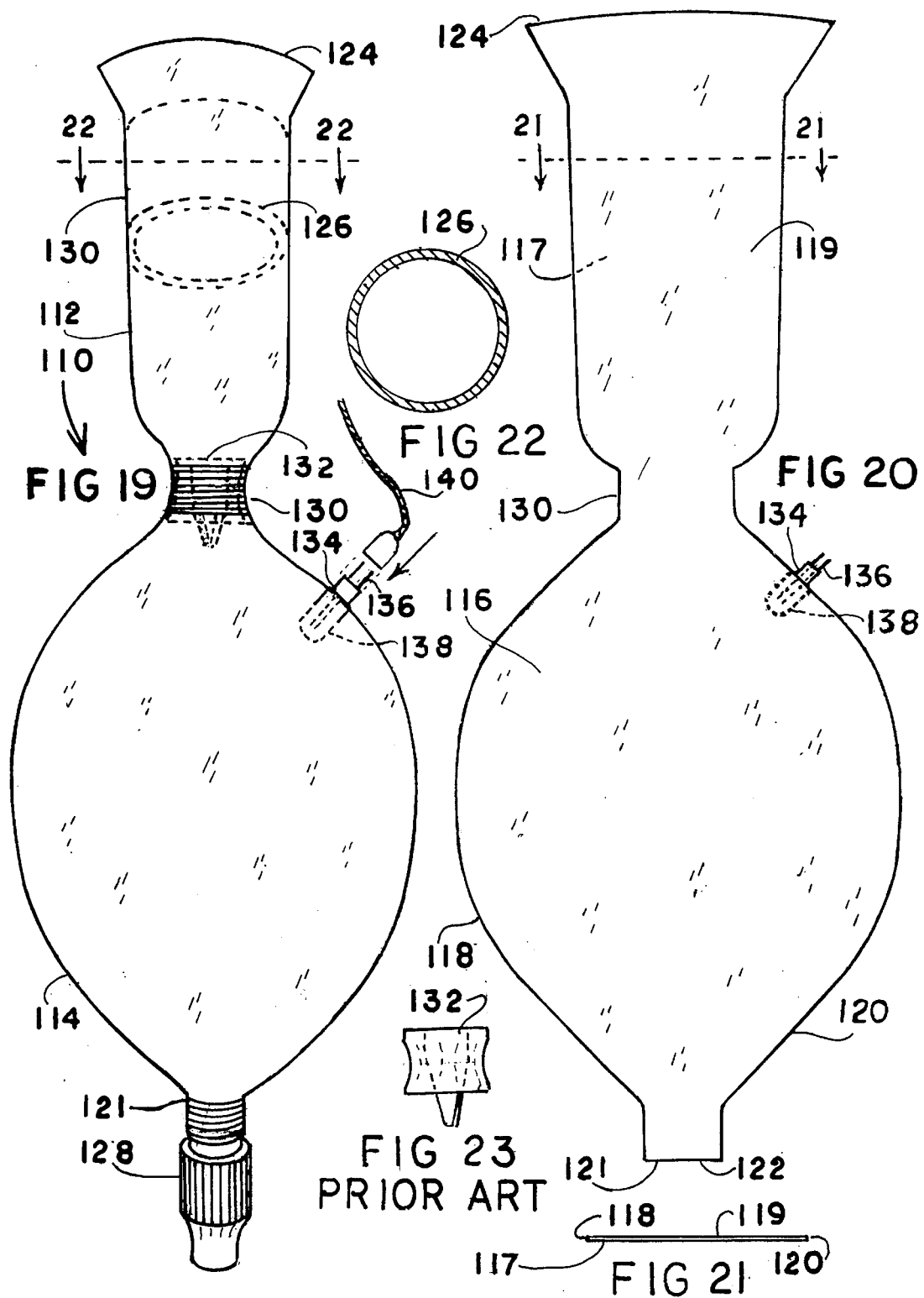

CONDOM CATHETER WITH IMPROVED VALVE AND RETAINING MEANS

BACKGROUND OF THE INVENTION

The present invention relates to male incontinence devices, in particular to a ribbed surface on the inside open end of the condom sheath portion to improve catheter adherence, an integrally made reinforced soft non-return valve between the sheath and the urine collecting compartment to prevent urine spillage, an alternative soft non-return, non-invertible two-valve assembly designed to prevent pooling. Also a garment which can be used to attach a catheter for use by spinal injured patients and an inexpensive non-elastomeric condom catheter with prior-art duck-bill non-return valve and a prior-art twist-around drain valve.

BACKGROUND—FIELD OF PRIOR ART

U.S. Pat. No. 5,380,312, dated Jan. 10, 1995, issued to Victor Goulter, and U.S. Pat. No. 5,009,649, dated Apr. 23, 1991, issued to Victor Goulter and Barbara Goulter, are incorporated by reference as part of the specification of this invention for details of construction for similar incontinence devices, which could be worn with comfort, which permitted the wearer to engage in most normal social and business activities, and which provided many other advantages including the avoidance of the skin-damaging and painful adhesives often used to keep devices in place.

There is however, one common problem with the above Goulter condom catheters, as well as with some other external catheter devices used in the managing of incontinence in men. The problem is their tendency to come off in use. This problem may be worsened by the shape of the user's penis. As is well known, penises come in a variety of shapes and sizes. If a man's glans exceeds the penile shaft in diameter, a condom device is more likely to stay in place, whereas if the penile shaft tends to taper toward the glans, and the glans is smaller in diameter than the shaft, such a device will be less secure. This is true both for circumcised and uncircumcised men. A more adherent condom catheter would tend to make the wearer more socially secure. By the same token, a more secure condom used for sexual purposes would be of substantial benefit in preventing both unwanted pregnancies and sexually transmitted diseases, notably AIDS. This device is addressed in a separate application. Further problems with the Goulter patent No. 5,380,312, specifically, related to the construction process and the use of a hard non-return valve. The hard valve had to be fitted into the completed sheath portion of the device, requiring a separate process which added to the cost of production. Also, if the device unintentionally came off the user after it had collected a quantity of urine, the pressure of the collected urine might force the hard non-return valve casing to invert, dislodging the hard valve and causing a spill. Additionally, a hard non-return valve tends to act as a catalyst, supporting the build-up of crystals from urine, possibly rending the valve ineffective and non-reusable while all other parts were still in functional condition. Yet another problem was a real if remote danger of injury if the hard-valve device were worn during certain activities; for example, if the valve were strongly impacted by a ball or another player during contact sports, it might bruise the penis.

The drain valve also presented problems, whether the pull-out plug or the screw-off cap were used. Men with shaky or arthritic hands or with impaired nerves might have difficulty replacing a plug or screwing a cap off and on. Some users also tended to get urine on their hands while draining the device. This last problem also affected nurses and other care-givers attending incapacitated or aged men.

A further problem: exists with prior-art incontinence catheters when used by certain patients who have suffered spinal injuries. Many such patients have no feeling from the waist down, and would there-fore not realize if they unintentionally fitted a catheter too tightly, creating danger of diminished blood circulation and possibly injury to the penis.

Another common problem with catheters which are attached and sealed to the penis, with or without adhesives, is that there is a tendency for some pooling to occur at the distal end of the sheath portion, due to a quantity of urine remaining collected in the cavity immediately in front of the penis plans. Since the collected urine in this area is frequently replaced with newly voided urine, it is unlikely that a condom catheter could ever be designed to drain so entirely that the penis head was left perfectly dry. However, it is preferred that the area be as well and thoroughly drained as possible.

A further problem is that some people are allergic to latex and there is no device resembling the Goulter device which is made of a non-allergic material.

OBJECTS AND ADVANTAGES

Accordingly, one object and advantage of the present invention is to provide a one-piece, condom-like, adhesive-free male urinary incontinence device which is less likely to slip off than prior art devices.

Another object and advantage is to provide a one-piece male urinary device with a soft non-return valve which can be made integrally with the device during manufacture and which does not require a separate additional part to be inserted during a separate process; also, a valve which will not invert and spill urine if the device should come off unexpectedly. Also, to provide a non-return valve which is less supportive of crystal build-up, and one which will not tend to create injury if forced into sudden, hard contact with the penis, as could happen during contact sports. A further object and advantage of the present invention is to provide means to drain away urine which tends to pool in the cavity adjacent the penis glans in prior art external condom catheters.

Still another object and advantage of the present invention is to provide an incontinence device having a drain valve which is neither a pullout plug nor a screw-off cap but one which can be operated with ease by care-givers or by users whose hands are imperfectly steady, with far less likelihood of getting urine on their fingers. This is especially important as some diseases may be transmitted through urine.

Another object and advantage of the present invention is to provide a urine incontinence external condom catheter device which can be attached to a simple harness, garment or brace to be worn by the user, which would retain the catheter in place without need for a hook-and-loop band as a retaining means. Such an apparatus would be especially suitable for spinal injury patients as well as others who have difficulty keeping an exterior urine collecting device securely in place due to the shape or size of the penis or to the user's overweight. A still further object and advantage is to provide a one-piece male incontinence device which can in particular be made more inexpensively from non-elastomeric plastics such as vinyl or similar non-elastic yet very pliable material which is less likely than latex to cause allergic reactions.

BRIEF DESCRIPTION OF THE DRAWINGS

FIG. 19 is a perspective view of a male urinary incontinence external catheter constructed from a non-elastomeric material such as vinyl.

FIG. 20 is a top view of two sheets of vinyl which are cut/welded to a pattern for fabrication of the catheter shown in FIG. 19.

FIG. 21 is a sectional view taken along the line 21—21 of FIG. 20, shown welded at its edges.

FIG. 22 is a sectional view taken along line 22—22 of FIG. 19.

FIG. 23 is a side perspective view of a casing supporting a Prior-Art duck-bill non-return valve used in the catheter shown in FIG. 19.

DETAILED DESCRIPTION FIG. 1

Figure 1:
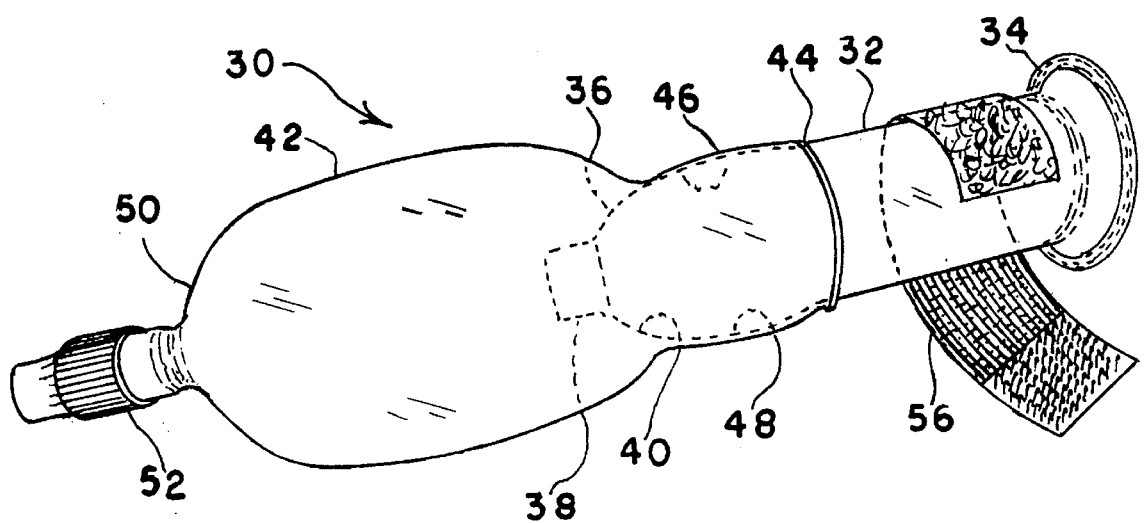
FIG. 1 is a perspective view of the condom catheter of the present invention made from an elastomeric material.

FIG. 1 shows a male urinary incontinence condom device 30 according to the invention. It can be made of an elastomeric material such as latex, silicon or polyisoprene or any other suitable material. The device consists of two main parts. The first part comprises an inner condom sheath 32, which has a graspable rim 34 at its open proximal end and a skin shield 36 incorporating a soft non-invertible non-return valve 38 at its distal or closed end 40; the second part is a urine-collecting compartment 42 having an open end 44 which is imperviously sealed at 46 to cylindrical portion 48 of inner condom sheath 32, and a closed distal end 50 which incorporates a Prior Art twist-around drain valve 52.

INNER CONDOM SHEATH—FIGS. 2-8

Inner condom sheath 32 can be made in several sizes to accommodate the needs of users. Most adult penises range from 20 mm (0.83") diameter to 40 mm (1.66"), the vast majority measuring between 23 mm (0.875") and 32 mm (1.25"). Since a snug fit is preferred in keeping the device securely in place, as well as in preventing urine leaks, it is desirable to make the catheters in several sizes. Each size is designated in mm and/or inches according to the diameter of the range of penises they are intended to accommodate.

MEANS FOR ADHERING CATHETER ONTO PENIS

In extended experiments and tests I have found that a series of very fine circular grooves and raised relief ribs 54 (FIG. 2 and 3) incised into the inside of the catheter at the proximal end have a positive effect in holding the device onto the penis. This effect can be further enhanced by adding some additional pressure by the use of an elastic hook and loop band 56 (FIG. 1).

Figure 2:
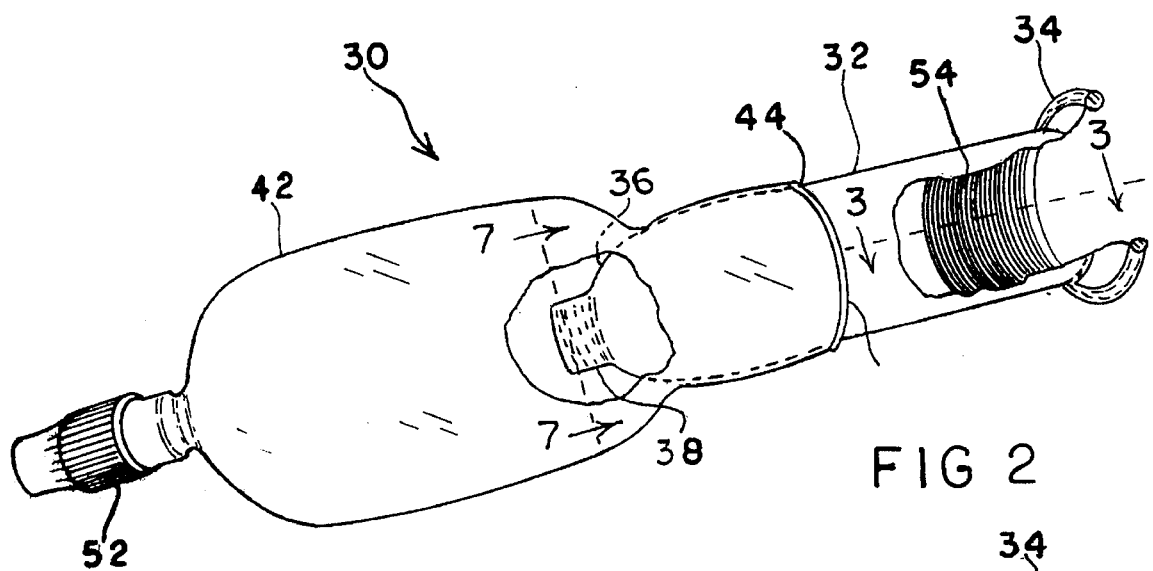
FIG. 2 is a perspective view of a condom catheter showing the open end of the condom sheath portion with part cut away to expose finely perspective view of a thread-reinforced non-return non-invertible soft valve.

When used for incontinence catheters, interior ribs 54 are about 0.5 mm (0.020") deep and are incorporated around the inside of the sheath starting near the open end; these are spaced at about 0.5 mm (0.020") apart, creating fine grooves in between. The width of the ribbed portion is approximately matched to the size of the device, such that about 28 mm of ribs are formed in a device measuring 28 mm in diameter, while approximately 31 mm width of ribs are molded into a 31 mm diameter device. A lesser or greater number of ribs per centimeter or inch can be used; i.e., the ribs can be 1 mm deep and 1 mm apart; however, it is preferred that the ribs be very closely spaced, as shown in FIG. 2. Also the length of the ribbed area can be increased or decreased.

The shape of the ribbing can add additional adherence; i,e., ribs that lean inwardly, as shown at 58 (FIG. 3), tend to be more adhering on a penis than ribs that would resemble the rounded shape of a screw thread (not shown). To obtain a lean-in type rib 58 (FIG. 3), a series of look-alike grooves (not shown) are machined around the proximal end of the mandrels (also called formers) to create the desired rib shape. The ribs in the catheters are produced integrally with the sheath when the mandrel is dipped into liquid latex and thereafter cured. Various other groove shapes and angles besides those shown at 58 in FIG. 3 can be designed; also different depths and spacings can be used to obtain different degrees of catheter adherence.

Figure 4:
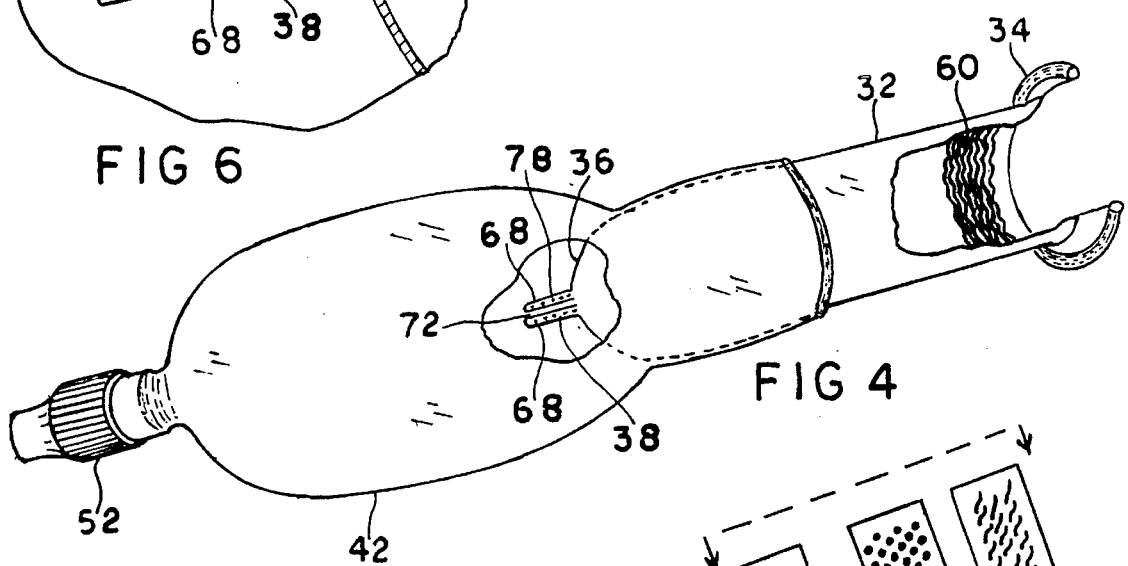
FIG. 4 is a cut-away view of the open end of the condom sheath portion showing an alternative relief structure to the ribbing shown in FIG. 2, and also a cut-away sectional view of the non-return valve used in the device.

Alternatively, a fine screw thread (not shown) can be machined into the mandrel in lieu of the series of fine separate ribs shown at 54 (FIG. 2). Another design is shown in FIG. 4, in which rows of circular grooves are combined to produce a pattern of waving lines 60 in raised relief. Other alternative designs besides the ribs shown in FIG. 2 can be used in relief to form gripping means; these would include circles of arcs placed 'face to face' and 'back to back' as shown at 62 (FIG. 5), or circles of small, closely spaced-apart protruding mounds 64, or circles of "S" shaped protrusions 66. The possible variety of such patterns is virtually infinite.

Figure 3:
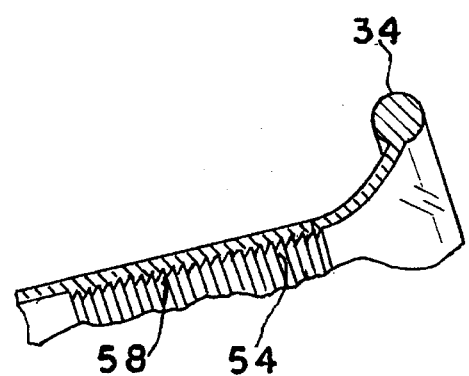
FIG. 3 is a perspective sectioned view taken along the line 3—3 of FIG. 2.
Figure 5:
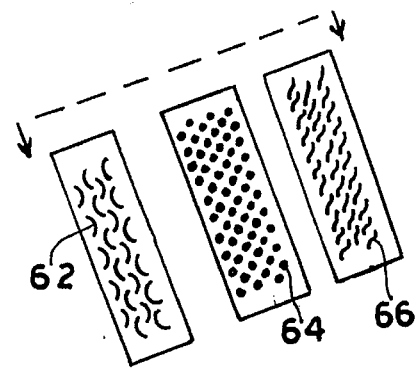
FIG. 5 are views of three samples of other relief structures which can be used in lieu of those shown in the cut-away view at the open end of the condom sheath portion of FIGS. 2 and 4.

Whether the gripping means is formed by a series of circular or helical ribs 54, as in FIG. 2, a pattern of waving lines 60, as in FIG. 4, or a pattern of mounds or protrusions 62, 64, 66, as in FIG. 5, the profile of the gripping means should be such that it forms a series of closely-spaced, skin-engaging edges as do the ramp-shaped, lean-in ribs 58 of FIG. 3. The skin-engaging aspect of the ribs 58 is provided in this illustrative example by the combination of a pointed peak and a steeply inclined or perpendicular distal face on some or all of the ribs 58. Features such as a pointed peak and/or a steeply inclined or perpendicular distal face can likewise be used to create skin-engaging edges in other raised relief pattern gripping means, such as those in FIGS. 4 and 5, to increase the adherence of the catheter to the wearer's penis.

INTEGRAL, NON-RETURN, NON-INVERTIBLE VALVE—FIGS. 1, 2, 4, 6–8.

Figure 6:
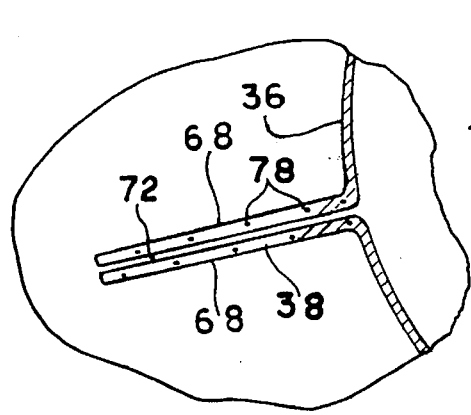
FIG. 6 is an enlarged sectional view of the non-return valve shown in a cut-away view of FIG. 4.
Figure 7:
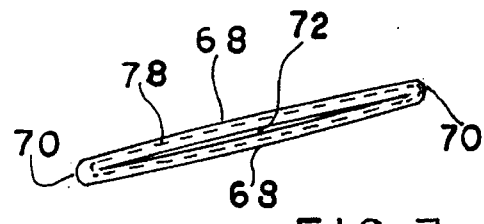
FIG. 7 is an enlarged end sectional view taken along the line 7—7 of FIG. 2.

FIG. 1, 2, 4 and 6 show a non-return valve 38, which allows urine from skin shield inner compartment 36 to pass without restriction into urine collecting compartment 42. This valve is formed around a double-edged, double-convex blade (described and illustrated in detail in FIGS. 10–14,) which protrudes from the lower end of the mandrel which produces skin shield 36, during the dipping process. It consists of two flaps 68 (FIG. 4), best seen in enlarged sectional view (FIG. 6). The two flaps are joined at their edges 70 (FIG. 7). Due to the double-convex cross sectional shape of the double-edged blade a permanent, partly-open slit 72 remains between flaps 68 (FIG. 7.)

Figure 8:
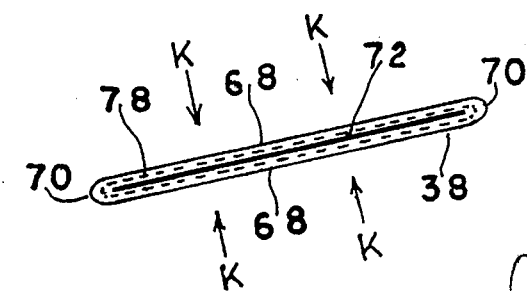
FIG. 8 is a sectional view of the valve shown in FIG. 7 illustrating the effect on the valve when pneumatic or hydraulic pressure is applied in the direction of arrows "K."

In use, when hydraulic or pneumatic pressure is applied to the exterior surfaces of flaps 68 in the direction of arrows "K" (FIGS. 8), as would exist if the user continued to urinate into the device and not timely empty the urine from the collection compartment. This pressure will exert a hydraulic pressure in the direction of arrows "K" and flaps 68 will immediately close together forming a seal as shown in FIG. 8. The seal is effective in preventing voided urine from flowing back through slit 72 to the opposite side of the skin shield.

NON-RETURN, NON-INVERTIBLE, VALVE CONSTRUCTION

The soft non-return valve as described above is preferred to a hard non-return valve in a condom catheter for the reason described in Description of Prior Art above. However, it is also necessary to make the soft valve, non-invertible in order to prevent urine spillage should the catheter inadvertently come off the penis. At the same time the valve must also retain its original flexibility so that it will close even when low pressure is applied from the collecting compartment, thus preventing voided urine from returning from the urine collecting compartment to the penis glans behind the skin shield. Making a non-return valve, also "non-invertible" has been achieved by reinforcing the latex in the valve itself with fine polyester or other suitable thread which is imbedded into the latex during manufacture. This is described below.

Figure 11:
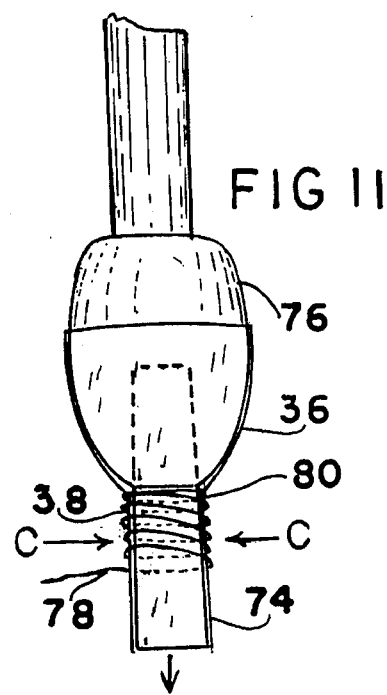
FIG. 11 is a perspective view of the mandrel shown in FIG. 10 with double-edged blade inserted, then dipped into liquid latex and a find thread wound around the blade.

A double-edged, double convex blade 74 (FIG. 10 and 13) is removably inserted into a corresponding cavity 81 (FIG. 10 and 12) in the lower end of mandrel 76. After dipping into liquid latex and curing, about seven to ten turns of fine polyester thread 78 (FIG. 11) is then wound around latex-covered blade 74 starting at base 80 and spiralling toward the distal end of the blade for about 15 mm (0.5") The mandrel and blade are then dipped again in latex which seals-in the polyester thread, and reinforces the non-return valve. Further heat curing and dipping is done until the latex is about 1 mm (0.040") thick. After curing blade 74 is withdrawn and valve 38 is cut to about 9 mm, (0.375") long, as shown at arrows C—C. (FIG. 11). The resulting non-return valve cannot invert simply because the reinforcing threads prevent slit 72 (FIGS. 4, 6–8) of the valve from opening sufficiently to allow the valve to invert through to the opposite side of the skin shield.

Alternatively valve 38 can be made non-invertable by using a latex rubber to which certain chemicals have been added which make the rubber harder and less elastic. However such valve is not as flexible, nor as responsive in operation when subjected to very low hydraulic back pressure from the urine in the collection compartment as a valve reinforced with thread only.

ONE-PIECE WITH NON-RETURN VALVE INSERTED THEREIN

Figure 14:
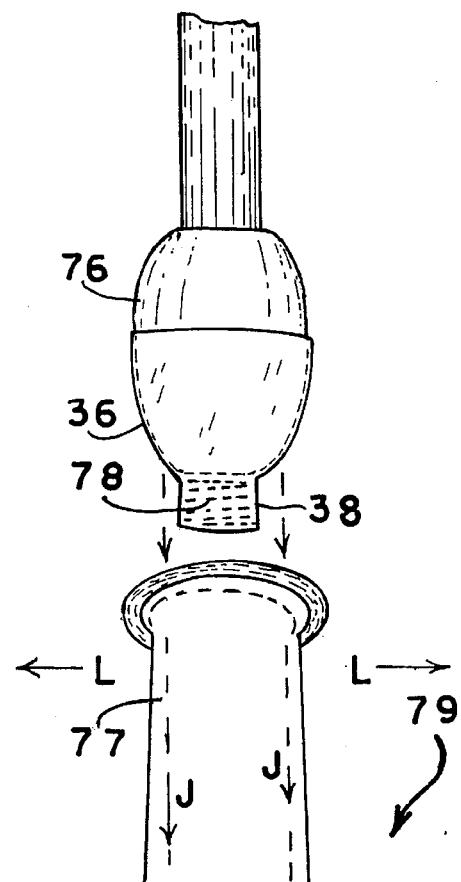
FIG. 14 is a perspective view of a single piece catheter into which a non-return, non-invertible valve is inserted and sealed inside the catheter.

FIG. 14 shows a one-piece catheter 79 into which mandrel 76, together with completed skin shield 36 and non-return, non-invertible valve 38 are inserted in the direction of arrows "J" and hermetically sealed in the position shown by broken line 82. Condom sheath portion 77 is stretched open in the direction of arrows "L" to facilitate entry of mandrel 76 into catheter 79 when fitting skin shield 35 and its non-return valve 38.

POOL DRAINING TECHNOLOGY EMBODIMENT FOR MALE EXTERNAL CATHETERS

Figure 15:
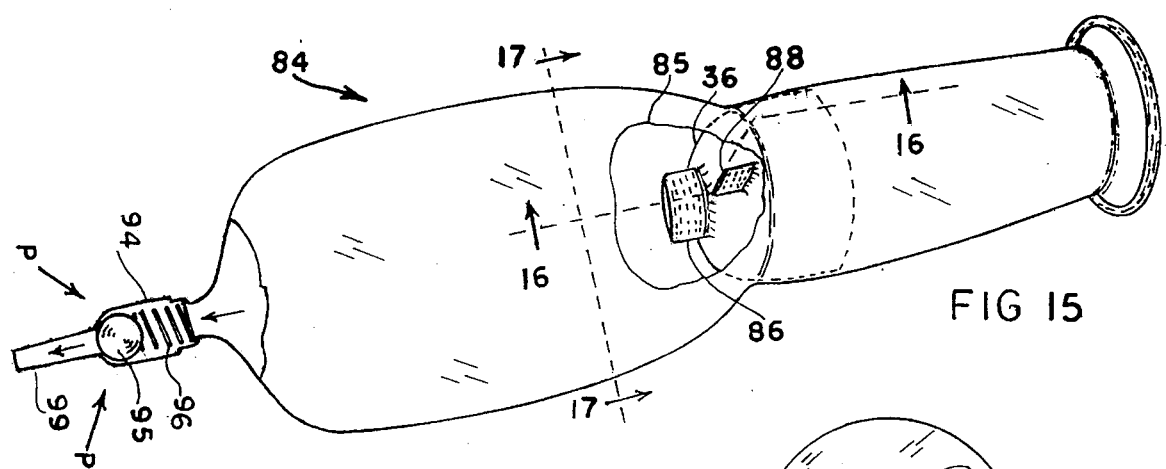
FIG. 15 is a top perspective view of a non-pooling two-valve assembly fitted to the skin shield inside a single piece catheter, which also has a ball-obturator drain valve/ disclosed in my U.S. Pat. No. 5,009,649) fitted to the urine collecting compartment.
Figure 16:
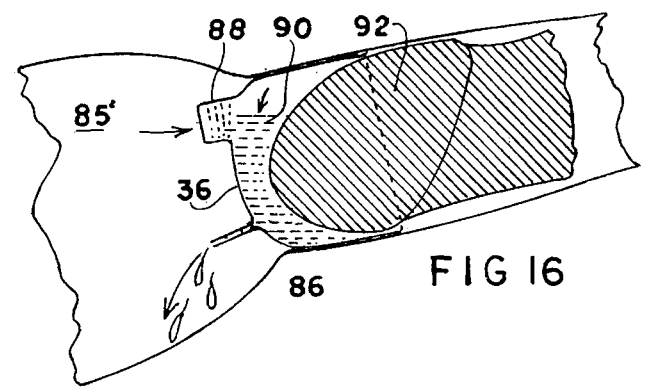
FIG. 16 is a sectional side view taken along the line 16—16 of FIG. 15.
Figure 17:
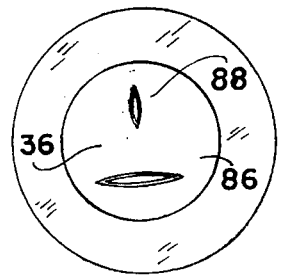
FIG. 17 is a cross sectional view taken along the line 17—17 of FIG. 15.

FIG. 15 shows a one-piece urinary incontinence condom catheter 84 fitted with pool draining means. The means comprises having two non-return, non-invertible soft valves 86 and 88 being positioned, one above the other on skin shield 36 (FIGS. 15, 16, and 17). FIG. 15 is a top perspective view of condom catheter 84, having a cut-away section 85 exposing one wide valve 86 positioned transversely across the lower side of skin shield 36, and one small valve 88 positioned vertically near the top side. FIG. 17 shows an end view taken along the line 17—17 of FIG. 15, which clearly shows transverse valve 86 positioned at the lower portion of skin shield 36 and vertical valve 88 positioned at the top portion of the shield. FIG. 16 is a side sectional view taken along line 16—16 of FIG. 15, showing a pool of urine 90 between penis glans 92 and skin shield 36.

DESCRIPTION OF POOL DRAINING TECHNOLOGY

When the user is urinating, pressure from the bladder forces the urine flow through the non-return valve into the urine collecting compartment. However, when urinating stops, a small quantity of urine may remain between the glans and the skin shield. This is known as pooling.

The following system is designed to drain the pool of urine into the collecting compartment, leaving the glans as dry as it is possible under these circumstances. An incontinence sufferer may be voiding urine almost continuously, or frequently, or occasional, or just sometimes, so it is unlikely that the penis glans will ever become completely dry in such an environment.

The system of draining the pool of urine is similar to that used to empty a can of liquid (soup) by puncturing two holes, one in either side of the lid; one hole allows air to enter the can, while the other allows the liquid to drain out until the can is empty.

A small upper vertical valve 88 (which is always slightly open unless under pressure) is provided for air from within urine collecting compartment 85, to bleed into the top of the pocket above the pool of urine and replace the voiding urine which flows out the lower valve. Without it, the pool of urine will not flow so freely through lower valve 86 even though it is partly open. With the small upper vertical valve present, however, air will bleed through this valve thereby allowing urine to flow outward through the lower valve until pool of urine 90 has drained away.

It will be realized that should the catheter inadvertently come off after collecting a quantity of urine, both valves will fully close, because a hydraulic pressure will then exist against the valves, due to the elastomeric material in the catheter, thereby preventing any spilling of voided urine.

FIG. 15 also shows a ball-obturator valve 94 which is disclosed in our U.S. Pat. No. 5,009,649, the entire disclosure of which is hereby incorporated by reference, and which can be used on any of the catheters which are constructed from elastomeric materials. The advantage of this valve over other drain valves is that it is a soft valve generally and it can be manufactured integrally with the urine collection compartment requiring only the inserting of a plastic ball 95 and a compression spring 96 to complete the valve.

The ball obturator valve requires only to be squeezed by the thumb and forefinger of one hand in the direction of arrows "P" to drain urine from the collecting compartment. This action will push the ball away from its seat, thereby allowing urine to flow. It can be made integrally with the collecting compartment and provided with an extended nozzle 99, so as to prevent urine coming into contact with the user's hand when operating the valve. The nozzle can be connected to an extension tube (not shown) using prior art tube connectors, and then to a bedside bag, or even to a leg bag.

PRIOR-ART TWIST-AROUND DRAIN VALVE—FIG. 9.

Figure 9:
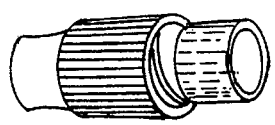
FIG. 9 is a perspective view of a prior-art screw-around on/off valve attached to the urine collecting compartment shown in FIGS. 1, 2, 4, and 14.
Figure 10:
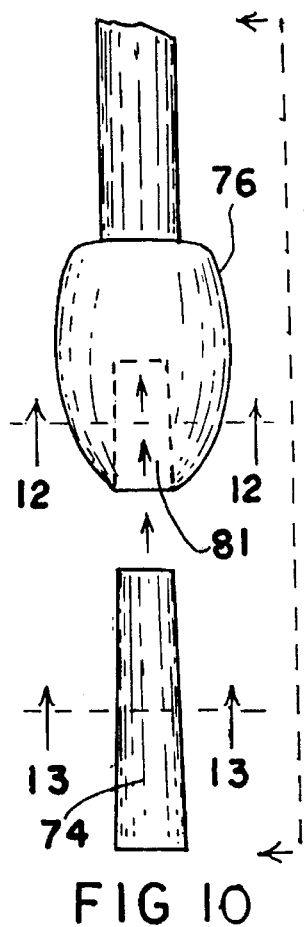
FIG. 10 is a perspective view of mandrel and removable double-edged blade used for manufacturing a non-return, non-invertible valve and skin shield.
Figure 12:
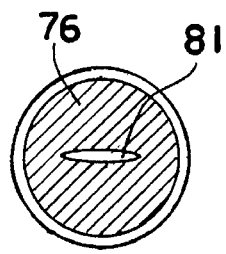
FIG. 12 is a sectional view taken along line 12—12 of FIG. 10.
Figure 13:
FIG. 13 is a sectional view taken along the line 13—13 of FIG. 10.

FIG. 9 shows a PRIOR-ART twist-around drain valve 52, which can be attached and imperviously sealed to any of the condom catheter embodiments in this application. When the catheter is made of latex and/or elastomeric material it is preferred that the material be made more substantial where the valve is to be inserted and sealed. When made of non-elastomeric material it is preferred that the valve be adhesively attached and imperviously sealed to the catheter material and in addition is bound around the outside with suitable thread cord and/or tape.

ALTERNATIVE MEANS FOR ATTACHING THE CATHETER TO THE WEARER—FIG. 18.

Figure 18:
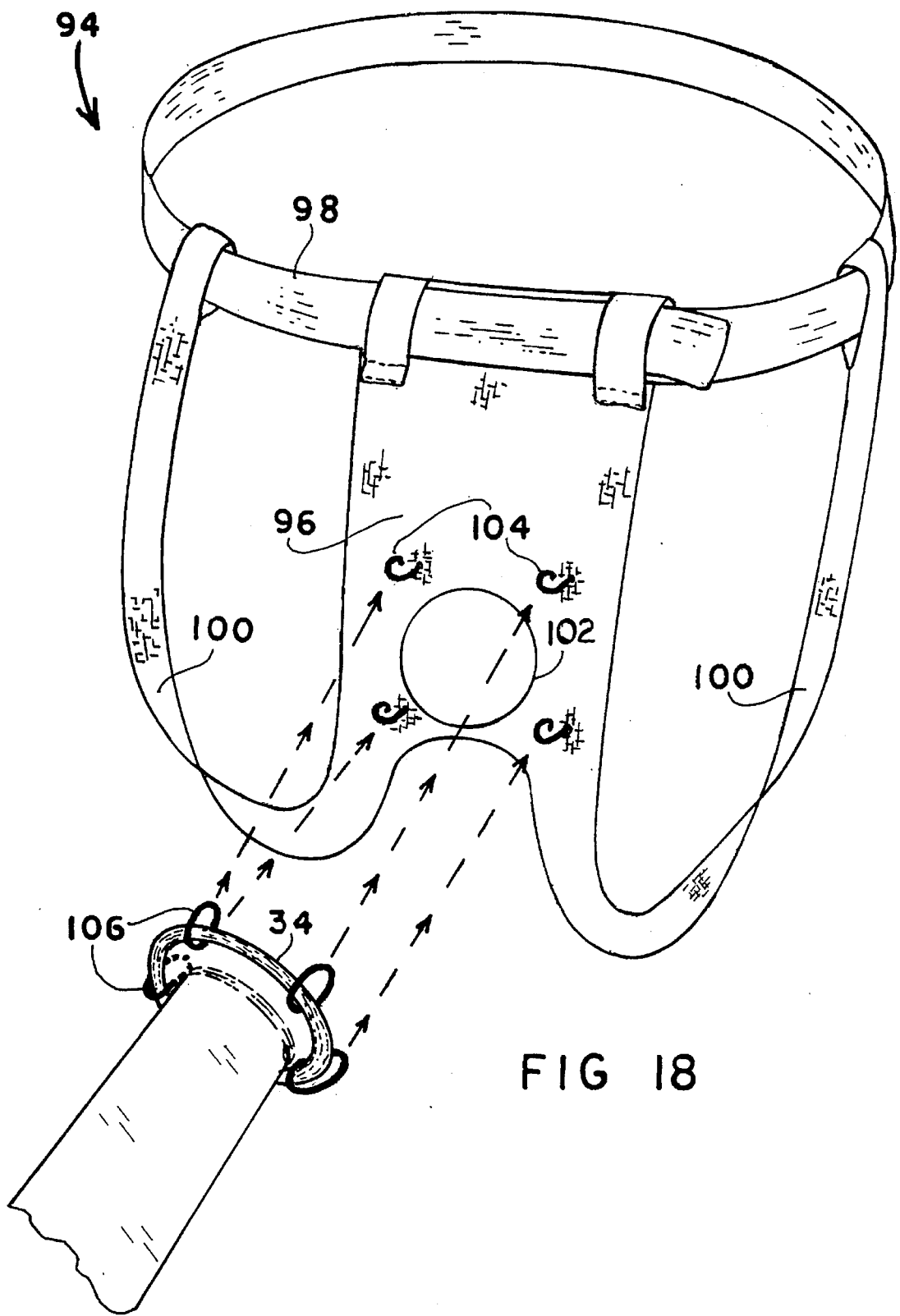
FIG. 18 is a perspective view of a garment which can be used by a spinal-injured person for anchoring a catheter of the present invention onto.

FIG. 18 shows a harness or garment 94 comprising a central bib portion 96, supported at its upper end by an elastic waist band 98 and at its lower end by leg straps 100. A circular hole 102 is provided through which the penis is placed when fitting the brace onto the wearer. Several hooks 104 are positioned in a circular manner around hole 102, in garment 94, such that when the catheter is fitted onto the user, rings 106 can be attached onto hooks 104, thereby retaining the catheter in place. Rings 106 can be of the split-link type clamped around graspable rim 34.

Alternatively, other means can be adapted to anchor the incontinence catheter to the garment, such as VELCRO hook and loop strips (not shown), one part attached to the catheter and the other to the garment.

DESCRIPTION OF NON-ELASTOMERIC CATHETER—FIGS. 19–24

FIG. 19 shows a one piece male urinary incontinence catheter 110 comprising a condom sheath 112 and a urine collecting compartment 114, according to another embodiment of the invention. This embodiment is made of non-elastomeric material such as vinyl, having such desirable properties as softness, pliability, water-resistance, puncture-resistance, non-allergic and conformity to both the wearer's body and his clothing. It can also be made of any similarly tough pliable material, which preferably can be instant heat-cut/welded using prior-art methods around a suitable pattern, as shown in FIG. 20.

FIG. 20 and 21 show a suitable pattern 116 comprising two layers 117 and 119 of plastic material such as vinyl, which are instant heat-cut/welded along edges 118 and 120. Edge 124 and 122 are cut but not welded, and provide an open proximal and distal end. Open proximal end 124 (FIG. 19) is fitted internally with a deformable plastic sleeve 126, such as foam plastic or the like, (FIG. 19 and 22) having a slightly larger internal diameter than the size of the penis for which it is intended to fit onto.

Narrow portion 130 (FIG. 19 and 20) of catheter pattern 116 provides a cylindrical aperture for fitting and imperviously sealing and binding thereto a prior art non-return valve 132, shown in FIG. 23. FIG. 19 shows non-return valve 132 imperviously sealed inside narrow portion 130 and externally bound in place.

A screw-around drain valve 128 is imperviously sealed in aperture 121 of catheter 110 for the user to drain urine into a men's urinal in a natural manner. It is also securely bound on the outside with tape or cord of any suitable type. It is recommended that VELCRO hook and loop bands (not shown) be used to close condom sheath 112, along with deformable plastic sleeve 126, snugly onto the penis.

In the event that a user is a spinal patient with impared feeling below the waist line and who is also allergic to latex materials, and needs to use a catheter made of vinyl, garment 94 (FIG. 18) can be used in conjunction with the vinyl catheter to removably attach it to the user. The catheter can be attached to the garment rings as shown in FIG. 18, or by the use of VELCRO hook and loop strips, or by prior-art adhesive strips.

Since a non-elastomeric material is used in this embodiment of my condom catheter, the urine collecting compartment will be non-extensible under pressure of continually voided urine, and such pressure could tend to push the catheter off the penis unless the compartment is timely emptied. This could be a real problem for users, especially for spinal injured patients.

This problem is overcome herewith by using a sound producing buzzer which sounds when the urine collecting compartment becomes full and needs to be drained, and is described in the following paragraph.

A prior-art pressure-sensitive electrical switch 134 is imperviously sealed into edge 120 (FIG. 19 and 20). Switch 134 comprises two parts, a small sealed elastomeric chamber 138 positioned inside urine collection compartment 114, and external connector pins 136 on the outside of the compartment. Pins 136 can be attached by leads 140 to a belt-mounted 'buzzer' (not shown) worn by the user. When pressure inside compartment 114 rises due to continued urination, pressure sensitive switch becomes switched 'on' thereby completing an electrical circuit and sounding the buzzer and alerting the user to drain the compartment.

The use of modified underwear as shown in my U.S. Pat. 5,009,649 is recommended to be used in conjunction with all embodiments of urinal incontinence condom catheters shown in this application.

SUMMARY, RAMIFICATION, and SCOPE

Thus the reader will see that I have provided a male incontinence device which is far superior to any prior art device, due in part to its soft non-return valve which not only can be made integrally with the condom catheter during the manufacturing process but which also lessens the possibility of injury to the wearer during physical activity. Because this valve is also non-invertible, it therefore will not spill urine if the catheter should inadvertently come off the user. In addition, the soft valve is less likely to act as a catalyst, causing the build up of crystals from urine and damaging the capacity of a non-return valve to prevent the penis from remaining in contact with voided urine. I have also provided an alternate dual soft valve system which would automatically release any pooling of urine which may remain after periods of urine flow from the penis.

I have also provided a more effective means for keeping the catheter on the penis of the wearer in the form of a very fine array of ribbing along the interior of the opening of the condom sheath portion. A fine ribbing is more effective in adhering to the penile skin than smooth surfaced latex. The slight pressure of an elastic hook-and-loop band applied around the proximal portion of the condom catheter adds to the adhesive effect of the fine ribbing, thereby making the device additionally secure.

In addition, I have provided a simple harness for use by spinal injury patients to wear as an alternative means of attaching the device to the penis in preference to the elastic hook and loop band which they might otherwise unintentionally overtighten, causing possible injury to their penis. I have also provided a non-return, non-invertible soft valve, which is far less likely to injure the penis during contact games, as well as being less costly to manufacture, and less likely to act as a catalyst in the build-up of unwanted crystals.

I have also provided an alternative catheter made of vinyl or other suitable material for use by those users who react allergically to latex materials, and which could be made less expensively. Additionally I have provided means for audibly elerting a user to drain a non-extensible urine compartment when it has reached capacity.

The devices disclosed herein are the result of the applicant's persistent determination over many years to return to normal life following prostatectomy and the resulting incontinence.

While the above description contains many specificities, the reader should not construe these as limitations on the scope of the invention, but merely as exemplifications of preferred embodiments thereof. Those skilled in the art will envision that many other possible variations are within its scope; for example, skilled artisans will readily be able to change the fineness of the ribbing, and/or the shape and angles and depth of the grooves. The possible configurations of the relief are virtually limitless, and the depth may also vary, as may the extension of the relief structure inside the length of the sheath portion.

The shape, width, length, or position of the non-return valve can be changed, or even the number of turns of thread, or type of thread material used. The size, shape and manner of attaching the twist-around drain valve are also variable. It is also possible to change the size, position or angle of the wide horizontal and small vertical valves, or even the type of valves used to reduce pooling of urine.

Other types of harness or braces can be envisioned for spinal injury patients to wear, and to which the catheter can be attached. Other attachment means can be provided for connecting the catheter to the braces, aside from the present rings and hooks; for example, hook and loop tabs fitted to the catheter and the bib portion, and or adhesive strips. Accordingly, the reader is requested to determine the scope of the invention by the appended claims and their legal equivalents, and not by the examples which have been given.

I claim:

1. A male incontinence device, comprising:

a first compartment sized to fit over the penis of a wearer, a second, urine-collecting compartment, a soft, non-invertable, non-return valve means connecting said first compartment to said second compartment for allowing fluid to flow from said first compartment to said second compartment and for preventing fluid from flowing from said second compartment to said first compartment, and wherein said soft, non-invertable, non-return valve means is prevented from inverting due to a pressure gradient from said second compartment to said first compartment, and a second valve means connecting said first compartment to said second compartment for allowing air to flow from said second compartment to said first compartment.

2. The male incontinence device of claim 1 wherein said first compartment has a friction-increasing surface on at least a portion of an interior surface of said first compartment.

3. The male incontinence device of claim 2 wherein said friction-increasing surface comprises a relief pattern on said interior surface of said first compartment.

4. The male incontinence device of claim 3 wherein said relief pattern comprises a pattern of alternating circumferential ribs and grooves on said interior surface of said first compartment.

5. The male incontinence device of claim 3 wherein said relief pattern comprises a pattern of raised relief structures.

6. The male incontinence device of claim 5 wherein said raised relief structures are selected from the group consisting of mounds, arc-shaped raised relief structures, and S-shaped raised relief structures.

7. The male incontinence device of claim 1 wherein said soft, non-invertible, non-return valve means comprises a flexible, tubular member having a proximal end attached to said first compartment and a distal end extending into said second compartment and a slit-shaped lumen therebetween, whereby a pressure gradient from said first compartment to said second compartment causes said slit-shaped lumen to open, allowing fluid to flow from said first compartment to said second compartment and a pressure gradient from said second compartment to said first compartment causes said slit-shaped lumen to close, preventing fluid from flowing from said second compartment to said first compartment.

8. The male incontinence device of claim 7 wherein said soft, non-invertible, non-return valve means further comprises a circumferential reinforcing fiber within a wall of said flexible, tubular member, whereby said flexible, tubular member is prevented from inverting due to a pressure gradient from said second compartment to said first compartment.

9. The male incontinence device of claim 1 further comprising a drain valve means connected to said second, urine-collecting compartment for draining fluid from said second, urine-collecting compartment.

10. The male incontinence device of claim 9 wherein said drain valve means is a twist valve selectively rotatable from a closed position to an open position.

11. The male incontinence device of claim 1 wherein said first compartment and said second, urine-collecting compartment are formed with a single, continuous exterior wall surrounding an interior chamber including said first compartment and said second, urine-collecting compartment, and a skin shield is bonded within said interior chamber to separate said first compartment from said second compartment.

12. The male incontinence device of claim 1 wherein said first compartment is formed with an open proximal end and a closed distal end and said second, urine-collecting compartment is formed with an open proximal end and a closed distal end, and wherein said proximal end of said second, urine-collecting compartment is bonded to said distal end of said first compartment.

13. The male incontinence device of claim 1 further comprising a graspable rim on a proximal end of said first compartment.

14. The male incontinence device of claim 1 further comprising a garment to be worn by the wearer and means for attaching a proximal end of said first compartment to said garment.

15. The male incontinence device of claim 14 wherein said means for attaching comprises at least one hook attached to said garment and at least one ring attached to said proximal end of said first compartment, whereby said proximal end of said first compartment is attached to said garment by engaging said at least one ring with said at least one hook.

16. The male incontinence device of claim 1 wherein said first compartment is made of an elastomeric material which conforms to the penis of the wearer.

17. The male incontinence device of claim 1 wherein said second compartment is made of an elastomeric material which expands to increase the capacity of said second compartment as it is filled with fluid.

18. A male incontinence device, comprising:
    a first compartment sized to fit over the penis of a wearer,
    a second, urine-collecting compartment,
    a first non-return valve means connecting said first compartment to said second compartment for allowing fluid to flow from said first compartment to said second compartment and for preventing fluid from flowing from said second compartment to said first compartment, and
    a second valve means connecting said first compartment to said second compartment for allowing air to flow from said second compartment to said first compartment.

19. The male incontinence device of claim 18 wherein said second valve means comprises a flexible, tubular member having a proximal end attached to said first compartment and a distal end extending into said second compartment and a slit-shaped lumen therebetween, whereby a pressure gradient from said second compartment to said first compartment causes said slit-shaped lumen to close, preventing fluid from flowing from said second compartment to said first compartment, and in the absence of a pressure gradient from said second compartment to said first compartment said slit-shaped lumen remains open to allow airflow therethrough.

20. The male incontinence device of claim 18, further comprising:
    a deformable sleeve positioned within said open proximal end between said first compartment and the penis of the wearer.

21. The male incontinence device of claim 20 wherein said first compartment and said second, urine-collecting compartment are made of a non-elastomeric material.

22. The male incontinence device of claim 20 further comprising a means for compressing said deformable sleeve onto the penis of the wearer.

23. The male incontinence device of claim 20 further comprising a garment to be worn by the wearer and means for attaching a proximal end of said first compartment to said garment.

24. The male incontinence device of claim 20 further comprising a means for detecting pressure within said second compartment and an alarm means for alerting the wearer of a rise in pressure within said second compartment.

25. The male incontinence device of claim 20 wherein said deformable sleeve substantially fills an annular space between said first compartment and the penis of the wearer.

26. The male incontinence device of claim 25 wherein said deformable sleeve is made of deformable plastic foam.

* * * * *

UNITED STATES PATENT AND TRADEMARK OFFICE
CERTIFICATE OF CORRECTION

PATENT : 5,618,277

DATED : April 8, 1997

INVENTOR(S) : Victor H. Goulter

It is certified that error appears in the above-identified patent and that said Letters Patent is hereby corrected as shown below:

Column 2, line 50: change "pullout", to --pull-out--.

Signed and Sealed this

Thirteenth Day of January, 1998

Attest:

BRUCE LEHMAN

Attesting Officer    Commissioner of Patents and Trademarks